United States Patent [19]
Robinson et al.

[11] Patent Number: 5,773,609
[45] Date of Patent: Jun. 30, 1998

[54] PHOTOACTIVATABLE COMPOSITIONS AND TO METHODS FOR THE DIAGNOSIS AND TREATING MEDICAL CONDITIONS

[75] Inventors: Byron Robinson; Alan R. Morgan; Hugh L. Narciso, Jr., all of Santa Barbara, Calif.

[73] Assignee: PDT Pharmaceuticals, Inc., Santa Barbara, Calif.

[21] Appl. No.: 801,831

[22] Filed: Feb. 14, 1997

Related U.S. Application Data

[62] Division of Ser. No. 508,238, Jul. 27, 1995.

[51] Int. Cl.$^6$ .......................... C07D 493/04; A61K 31/35
[52] U.S. Cl. .......................... 540/145; 540/122; 540/450; 514/455; 549/385; 549/387; 549/282
[58] Field of Search .................................. 549/387, 385, 549/282; 540/145, 450; 514/455

[56] References Cited

U.S. PATENT DOCUMENTS

| | | | |
|---|---|---|---|
| 5,116,864 | 5/1992 | March et al. | 514/455 |
| 5,200,425 | 4/1993 | Goupil | 549/282 |
| 5,256,648 | 10/1993 | Gasparro et al. | 514/44 |
| 5,284,869 | 2/1994 | Bisaccia et al. | 514/455 |

OTHER PUBLICATIONS

Gasparro et al., Photochem. Photobiol. 1993, 57(6): 1007–1010.

*Primary Examiner*—Mukund J. Shah
*Assistant Examiner*—Pavanaram K. Sripada
*Attorney, Agent, or Firm*—Michael G. Petit

[57] ABSTRACT

A broad class of photosensitive compounds having enhanced in vivo target tissue selectivity and versatility in photodynamic therapy. Many furocoumarin compounds, such as psoralens, exhibit cytostatic activity when photoactivated but exhibit little in vivo specificity for selectively accumulating in any particular target tissue such as atheromatous plaques. Reactive Oxygen Producing Photosensitizers ("ROPPs") are photoactivatable compounds having an affinity for hyperproliferating cells (such as atheromatous plaque cells), which when photoactivated, produce cytotoxic reaction products. The photoactivity of a ROPP, such as a porphyrin, may be reduced by metalating the porphyrin while the selective affinity of the metalized ROPP for hyperproliferating tissue remains substantially unchanged. By linking a furocoumarin compound to a ROPP to form a F-ROPP, the cytostatic properties of the furocoumarin portion of the F-ROPP can be exploited while the selective affinity of the ROPP portion of the compound for hyperproliferating cells such as atheromatous plaque provides enhanced tissue selectivity without cytotoxicity. In vivo, certain F-ROPPs may be forced to selectively accumulate in a target tissue by illuminating only the target tissue with light having a wavelength operable for photoactivating the F portion of the F-ROPP thereby causing the F-ROPP to either form a monoadduct with or crosslink the cellular DNA in the target tissue. Light of a second wavelength can then be delivered to the target tissue to photoactivate the ROPP portion causing further interference with cellular activity.

5 Claims, 3 Drawing Sheets

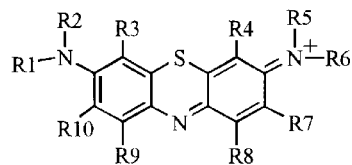
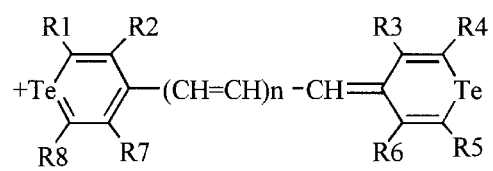
FIGURE 13    FIGURE 14
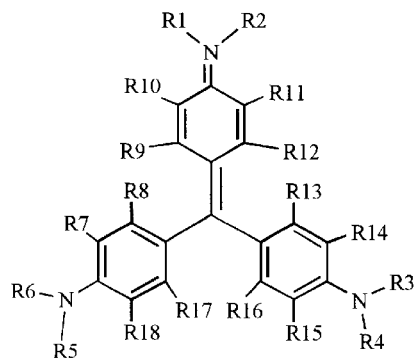
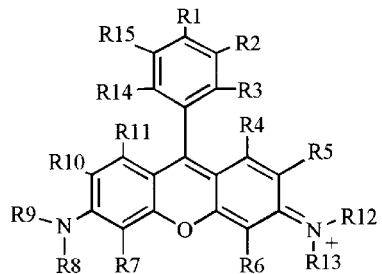
FIGURE 15    FIGURE 16
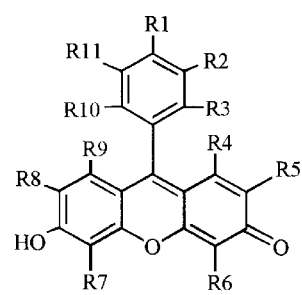
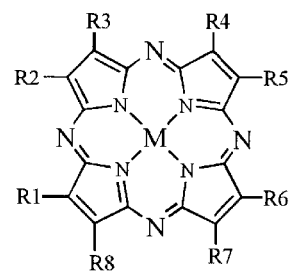
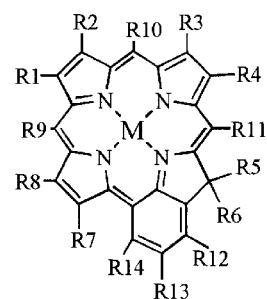
FIGURE 17    FIGURE 18    FIGURE 19
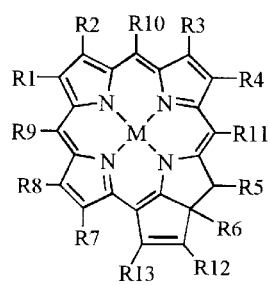
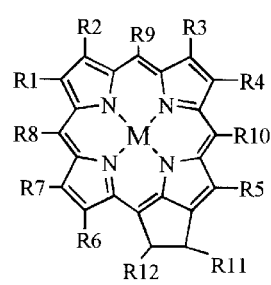
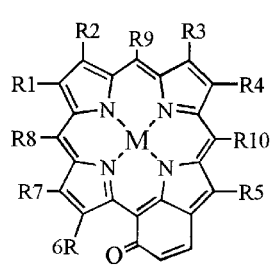
FIGURE 20    FIGURE 21    FIGURE 22

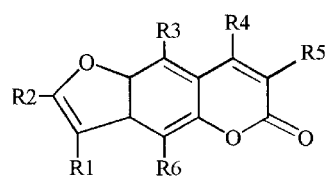
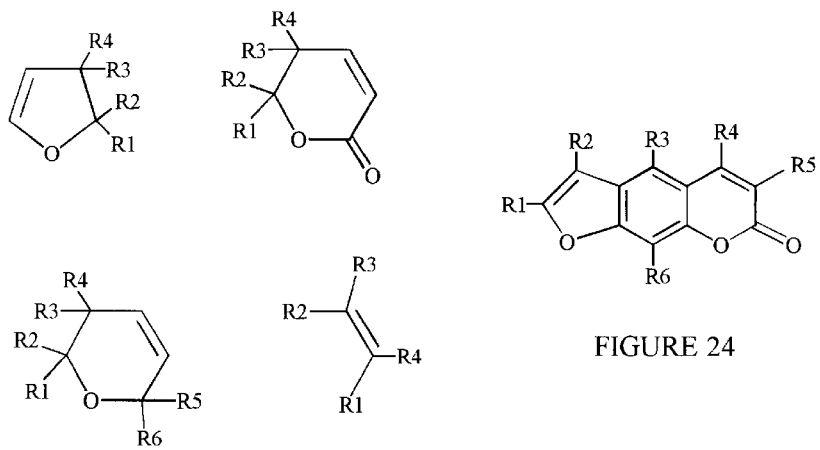
FIGURE 23
FIGURE 24
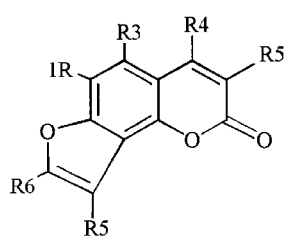
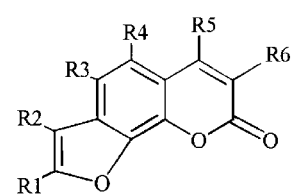
FIGURE 25
FIGURE 26
FIGURE 27
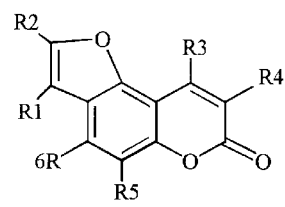
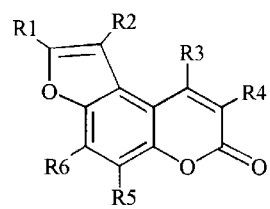
FIGURE 28
FIGURE 29

PHOTOACTIVATABLE COMPOSITIONS AND TO METHODS FOR THE DIAGNOSIS AND TREATING MEDICAL CONDITIONS

REFERENCE TO RELATED APPLICATIONS

This application is a divisional of co-pending U.S. patent application Ser. No. 08/508,238 filed Jul. 27, 1995.

BACKGROUND OF THE INVENTION

1. Field of the Invention

This invention relates to photoactivatable compositions and to methods for using the compounds for diagnosing and treating medical conditions.

2. Prior Art

Photodynamic Therapy (PDT) is used for treating various diseases including cancer, psoriasis, vascular disease, non-cancerous hyperplastic disease such as benign prostatic hyperplasia, macular degeneration, glaucoma, and certain viral infections. PDT requires concentrating a photosensitizer drug in a target tissue then photoactivating the compound with a device which includes a light source providing light at a particular wavelength and power level. The drugs administered for PDT are commonly known as photosensitizers (PS) due to their inherent ability to absorb photons of light and transfer that energy to oxygen which then converts to a cytotoxic or cytostatic species. Table 1 presents a list of classes of photosensitizer compounds commonly employed in PDT, which PS's are referred to hereinafter in the alternative as "ROPPs" (Reactive Oxygen Producing Photosensitizer molecules) and "LEPs" (Light Emitting Photosensitive molecules). While not exhaustive, the list of PDT photosensitizer drugs presented in Table 1 is exemplary of the variety of ROPPs and LEPs currently used in the art.

The photoactivating device employed for PDT usually comprises a monochromatic light source such as a laser, the light output of which may be coupled to an invasive, light delivery catheter for conduction and delivery to a remote target tissue. Such interventional light delivery catheters are well known in the art and are described, for example, in U.S. Pat. Nos. 5,169,395; 5,196,005; and 5,231,684. Other devices which are frequently used in conjunction with a light source and light delivery catheter include drug delivery devices and/or a balloon perfusion catheter (U.S. Pat. No. 5,213,576) and/or various medicament-dispensing stents for the slow localized release of the photosensitizer. PDT is presently an approved procedure in Canada, Japan, and The Netherlands for the treatment of various cancers.

In addition to cancer therapy, PDT is being tested for the treatment of psoriasis. Extra-corporal PDT of blood is being evaluated for the prevention of intimal hyperplasia following transplant surgery. PDT is also being evaluated for the treatment of vascular disease; most commonly the prevention of intimal hyperplasia following angioplasty. ROPPs are presently in clinical trials for the treatment of cutaneous cancers such as basal cell carcinoma, basal cell nevus syndrome, squamous cell carcinoma, and AIDS related Kaposi's sarcoma. ROPPs are also being investigated for the treatment of a cancer precursor, Barrett's esophagus. In addition, ROPPs may have utility for treating invasive cancers, cancer precursors, psoriasis, non-cancerous urological disorders, viral inactivation, macular degeneration, glaucoma and various vascular diseases.

TABLE 1

ROPPs and LEPs

Pyrrole-derived macrocyclic compounds
Naturally occurring or synthetic porphyrins and derivatives thereof (1)*
Naturally occurring or synthetic chlorins and derivatives thereof (2)
Naturally occurring or synthetic bacteriochlorins and derivatives thereof (3)
Synthetic isobacteriochlorins and derivatives thereof (4)
Phthalocyanines and derivatives thereof (5)
Naphthalocyanines and derivatives thereof (6)
Porphycenes and derivatives thereof (7)
Porphycyanines and derivatives thereof (8)
Pentaphyrin and derivatives thereof (9)
Sapphyrins and derivatives thereof (10)
Texaphyrins and derivatives thereof (11)
Phenoxazine dyes and derivatives thereof (12)
Phenothiazines and derivatives thereof (13)
Chalcoorganapyrylium dyes and derivatives thereof (14)
Triarylmethanes and derivatives thereof (15)
Rhodamines and derivatives thereof (16)
Fluorescenes and derivatives thereof (17)
Azaporphyrins and derivatives thereof (18)
Benzochlorins and derivatives thereof (19)
Purpurins and derivatives thereof (20)
Chlorophylls and derivatives thereof (21)
Verdins and derivatives thereof (22)

*(m) refers to the compound having molecular structure indicated at (m) in the specification where m is an integer between 1 and 22.

BRIEF DESCRIPTION OF THE DRAWINGS: see FIGS. 1–29

ROPPs and LEPs such as those indicated in Table 1, and as illustrated in FIGS. 1–23, have been shown to selectively accumulate, both in vitro and in vivo, in catheter induced atheromatous plaques in rabbit and swine models as evidenced by laser induced fluorescence and chemical extraction (H L Narciso, et al, Retention of tin ethyl etiopurpurin (SnET2) by atheromatous plaques: Studies in vitro & in vivo rabbits, *Proceedings of SPIE: Diagnostic and Therapeutic Cardiovascular Interventions IV,* 1994, 2130:30–41). In vitro studies utilizing human cadaver aortas demonstrate the passive accumulation of photosensitizers such as ROPPs and LEPs into naturally occurring atheromatous plaques. Certain ROPPs and LEPs have the ability to penetrate the nuclear membrane within a cell and to intercalate into the nuclear DNA, particularly ROPPs bearing a positive charge (cationic).

Psoralen-type compounds have also been investigated for their ability to prevent intimal hyperplasia. Psoralens and other furocoumarins (furane fused to coumarin and derivatives thereof) are also photosensitive compounds which have been used in the treatment of psoriasis for over 40 years. Such psoralen-based phototherapy is alternatively referred to herein as PUVA; Psoralen activated with UltraViolet A light. An exemplary list of some furocourmarin compounds is presented in Table 2. Systemically administered psoralen-type compounds penetrate the nuclear membrane of cells and may intercalate with the nuclear DNA in target tissue cells. Following intercalation with the target tissue's nuclear DNA, the psoralen compound is photoactivated with ultraviolet light or short wavelength visible light (see, for example, F P Gasparro, et al, The excitation of 8-Methoxypsoralen with visible light: Reversed phase HPLC quantitation of monoadducts and cross-links, *Photo-* chem. Photobiol., 1993, 57(6):1007–1010.), which UV light is preferably delivered only to the target tissue by a light delivery catheter or similar delivery device, to cause DNA crosslinking and ultimately a mutagenic effect in the cells comprising the target tissue. (K L March, et al, 8-Methoxypsoralen and longwave ultraviolet irradiation are a novel antiproliferative combination for vascular smooth muscle, *Circulation,* 1993, 87:184–91; BE Sumpio, et al, Control of smooth muscle cell proliferation by psoralen photochemotherapy, *J. Vasc. Surg,* 1993, 17:1010–1018; K W Gregory, et al, Photochemotherapy of intimal hyperplasia using psoralen activated by ultraviolet light in a porcine model, *Lasers in Surg. Med.,* 1994, (Suppl 6):12 Abstract).

Furocoumarins are photochemical agents showing potential for both diagnostic and therapeutic applications in medicine. The DNA cross-linking by furocoumarins such as described above proceeds by a two step process. Following injection of the fuorocoumarin into the body of an animal, the (planar) furocoumarin molecule first intercalates within the double helix of intracellular DNA or RNA. Following intercalation, the covalent addition of the furocoumarin to the polynucleic acid is achieved through the addition of light energy within the absorption band of the specific furocoumarin. Either furocoumarin -RNA or -DNA monoadducts or cross-links may be created upon illumination of the intercalated species. By forming covalent cross-links with base-pair structures, furocoumarins can alter the metabolic activity of a cell and induce cytostasis (G D Cimino, H B Gamper, S T Isaacs, J E Hearst, Psoralens as photoactive probes of nucleic acid structures and function: Organic chemistry and biochemistry, *Ann. Rev. Biochem.,* 1985, 54:1154–93).

TABLE 2

Furocoumarins‡

Compounds containing Furocoumarin sub-components (23)*
Psoralens and derivatives thereof (24)
Isopsoralens (angelicins) and derivatives thereof (25)
Pseudopsoralens and derivatives thereof (26)
Pseudoisopsoralens and derivatives thereof (27)
Allopsoralens and derivatives thereof (28)
Pseudoallopsoralens and derivatives thereof (29)

*(m) refers to the compound having the structure indicated at FIG. m in the appended figures where m is an integer $23 \leq m \leq 29$.
‡The furocoumarins may be either naturally occurring or synthetic.

Coronary artery disease is thought to be initiated by a disruption of fatty streaks which form early in life on the vessel wall which disruption, in turn, promotes thrombus formation. Over time the thrombus becomes organized and provides structure for the accumulation of fatty lipids, foam cells, cholesterol, calcium, fibrin, and collagen. A fibrous cap forms over this collection of lipid-rich material. Periodically this fibrous cap ruptures; releasing some of the lipid-rich material and exposing the remaining plaque materials to the circulating blood. Growth factors within the blood initiate the migration of smooth muscle cells (SMCs), from the media to the intima where proliferation of the SMCs begins. The ulcerated plaque induces the deposition of platelets and thrombus formation in a "response to injury" mode. This cycle recurs until eventually the plaque ruptures, the distal coronary artery is occluded by an thrombus and a heart attack occurs (V. Fuster, et al, Clinical-Pathological Correlations of Coronary Disease Progression and Regression, *Supplement to Circulation, Vol.* 86, No. 6, 1992:III-1-III-11 and J J Badimon, Coronary Atherosclerosis. A Multifactorial Disease, *Supplement to Circulation, Vol.* 87, No. 3, 1993:II-3-II-16).

Restenosis occurs when coronary disease is treated with an interventional therapy such as Percutaneous Transluminal Coronary Angioplasty, PTCA, or atherectomy, or laser angioplasty, or stenting, or a myriad of newer technologies. Restenosis refers to the over-aggressive autogenous repair of an injury to a blood vessel by the body. Intimal hyperplasia or the hyperproliferation of medial (and possibly adventitial) smooth muscle cells (SMCs,) is a major contributing factor to restenosis. Hyperproliferating SMCs form a neo-intima which can reduce the bore of the arterial lumen and thus the capacity of the artery to deliver oxygen rich blood. This reduction in cross-sectional luminal area can be more severe than the original constricted area which was treated. The foregoing problems are representative of some medical conditions which the compounds of the present invention may have particular application.

DNA cross-linking by furocoumarins results in the reduction of smooth muscle cell (SMC) proliferation and, since their DNA cross-linking activity is cytostatic, furocoumarins may have certain advantages over cytotoxic photosensitizers (ROPPs and LEPs) in the prevention of intimal hyperplasia as described by March, et al, U.S. Pat. No. 5,116,864 and Deckelbaum, et al, U.S. Pat. No. 5,354,774 the teachings of which patents are incorporated herein by reference thereto. The cytotoxicity of ROPPs and LEPs currently used in PDT results in the extravasation of intracellular organelles, cytoplasm, and cytokines which, in turn, elicits an inflammatory response. The inflammatory response elicited by extravasation of cellular contents is hypothesized as a key contributing factor to restenosis. The disadvantage of employing psoralens to prevent restenosis (when compared to photosensitizers such as ROPPs and LEPs) is that psoralens do not exhibit a selective affinity for atheromatous plaques over normal intimal tissue.

SUMMARY OF THE INVENTION

It is a primary object of the present invention to provide a photoactivatable compound which can be used to treat a variety of diseases.

It is an object of the present invention to provide a photoactivatable therapeutic compound which causes cytostasis but not cytolysis when bound to a cell and activated with light.

It is another object of the present invention to provide a photoactivatable compound which has a selective affinity for rapidly proliferating cells.

It is still a further object of the present invention to provide a photoactivatable compound which will reduce the incidence of restenosis following phototherapy of atheromatous plaque.

It is a further object of the present invention to provide a photoactivatable compound which can cause cytostasis when activated by a specific wavelength of light.

It is still a further object of the present invention to provide a photoactivatable compound which can cause cytostasis when activated by one particular wavelength of light and cause cytolysis when activated with light having a different wavelength.

It is yet a further object of the present invention to provide a method for treating such diseases as atherosclerosis, restenosis, cancer, cancer precursors, noncancerous hyperproliferative diseases, psoriasis, macular degeneration, glaucoma and viruses employing photoactivatable compounds.

It is a further object of the present invention to provide a method for employing such photoactivatable compounds for diagnosing such diseases as atherosclerosis, restenosis, cancer, cancer precursors, noncancerous hyperproliferative diseases, psoriasis, macular degeneration, glaucoma and viruses.

The features of the invention believed to be novel are set forth with particularity in the appended claims. However, the invention itself, both as to composition and manner of use, together with further advantages of these compounds may best be understood by reference to the following description of preferred embodiments.

DESCRIPTION OF THE PREFERRED EMBODIMENTS

Figure 1:
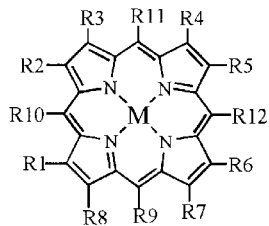
Figure 2:
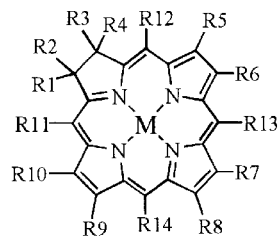
Figure 3:
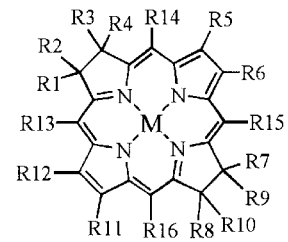
Figure 4:
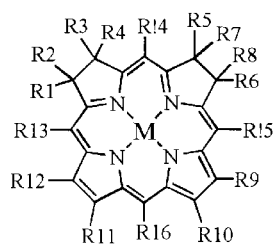
Figure 5:
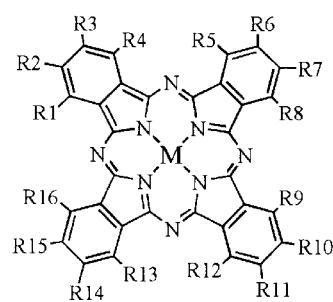
Figure 6:
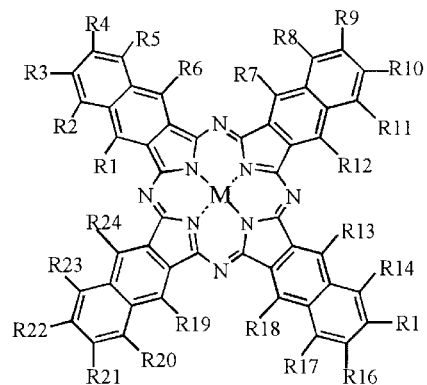
Figure 7:
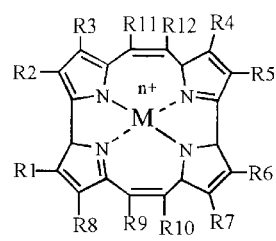
Figure 8:
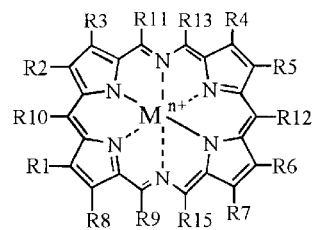
Figure 9:
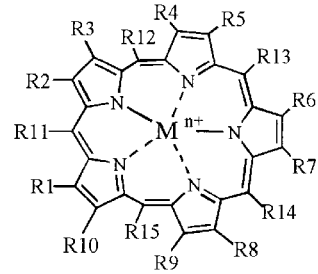
Figure 10:
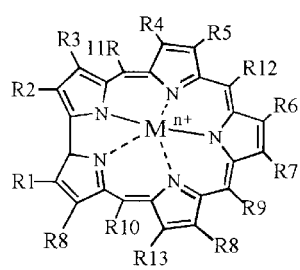
Figure 11:
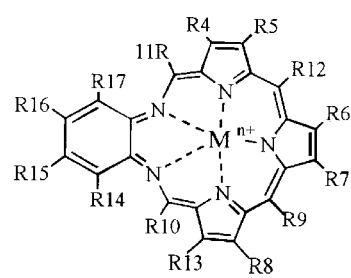
Figure 12:
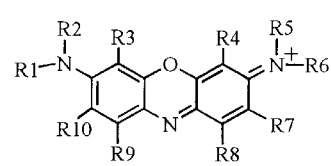

A problem encountered when using conventional cytotoxic photosensitizer compounds such as those listed in Table 1 for PDT is the post-administration inflammatory sequella such as restenosis of a blood vessel. While photosensitizers such as ROPPs and LEPs exhibit enhanced selectivity and avidity for rapidly proliferating cells in comparison with normal, more quiescent cells, the cytotoxic and cytolytic activity of such compounds may be undesirable.

A problem encountered when using PUVA for the treatment of hyperproliferative conditions is that furocourmarins exhibit little, if any, specificity and avidity for hyperproliferative cells over normal cells. Notwithstanding the foregoing, furocourmarins have the advantage that upon photoactivation with light they may either form a monoadduct to DNA or crosslink the nuclear DNA, thereby rendering the cell quiescent. Such cytostatic activity does not produce inflammation to the same extent as PDT employing ROPPs and LEPs. A novel class of photosensitizer compounds exhibiting the enhanced specificity of ROPPs and LEPs for hyperproliferating cells and the photocytostatic activity of furocourmarin compounds is described.

The compounds of the present invention form a super-class of compounds characterized by a furocoumarin compound or component thereof, alternatively referred to hereinafter as "F", conjugated with one or more of the following photosensitive molecules: (a) a ROPP (Reactive Oxygen Producing Photosensitizer) or a component thereof; or (b) a LEP (Light Emitting Photosensitizer) or a component thereof to form a F-ROPP or F-LEP. The individual compounds within this super-class of compounds are useful for the diagnosis and treatment of a myriad of diseases as previously described. F-ROPPs contained within this super-class of compounds are classes of compounds containing all possible combinations of any of the compounds set forth in Table 1 conjugated to compounds listed in Table 2. Additional compounds not explicitly listed in Tables 1 and 2 which exhibit the photosensitive and/or tissue specificity properties exemplified by ROPPs or LEPs conjugated to furocoumarins (F-ROPPs) should be construed as included within, and part of, this super-class of compounds. Each class of compound contains a plethora of specific compounds differing only in the particular functional groups attached to the basic structure.

For example, furocoumarins and derivatives thereof can be conjugated with porphyrins, chlorins, bacteriochlorins, isobacteriochlorins, phthalocyanines, naphthalocyanines, porphycenes, porphycyanines, pentaphyrin, sapphyrins, texaphyrins, phenoxazine dyes, phenothiazines, chaloorganapyrylium dyes, rhodamines, fluorescenes, azoporphyrins, benzochlorins, purpurins, chlorophylls, verdins and triarylmethanes and derivatives thereof, thereby creating 23 new classes of compounds. Compounds within each class are conveniently referred by first specifying the particular furocoumarin followed by the particular ROPP or LEPP. For example, isopsoralen conjugated with chlorin would be isopsorachlorin.

As a further example, furocoumarins such as naturally occurring or synthetic psoralens, as well as derivatives thereof, can be conjugated with one of the following photosensitive compounds from Table 1: porphyrins, chlorins, bacteriochlorins, synthetic isobacteriochlorins, phthalocyanines, naphthalocyanines, porphycenes, porphycyanines, pentaphyrin, sapphyrins, texaphyrins, phenoxazine dyes, phenothiazines, chaloorganapyrylium dyes, rhodamines, fluorescenes, azoporphyrins, benzochlorins, purpurins, chlorophylls, verdins and triarylmethanes, as well as derivatives of such photosensitizers. The foregoing conjugates form new classes of compounds which may conveniently be referred to, for example, as: Psoraporphyrins, Psorachlorins, Psorabacteriochlorins, Psoraisobacteriochlorins, Psoraphthalocyanines, Psoranaphthalocyanines, Psoraporphycenes, Psoraporphycyanines, Psorapentaphyrin, Psorasapphyrins, Psoratexaphyrins, Psoraphenoxazine dyes, Psoraphenothiazines, Psorachaloorganapyrylium dyes, Psorarhodamines, Psorafluorescenes, Psoraazaporphyrins, Psorabenzochlorins, Psorapurpurins, Psorachlorophylls, Psoraverdins, and Psoratriarylmethanes, and derivatives thereof, respectively.

The following examples presenting the synthesis of particular photosensitizer compounds in accordance with the present invention are representative of the variety of photoactive furocourmain-photosensitizer conjugates which can be made and the conditions therefor.

EXAMPLE 1

Pyropheophorbide linked 8-MOP. (8-MOP PPhe)

Pyropheophorbide (300 mg) was dissolved in dry tetrahydrofuran (100 mL) and 1,3-dicyclohexylcarbodiimide (100 mg) and dimethylaminopyridine (100 mg) were added. After stirring at room temperature for 15 min., a solution of 5-aminomethyl-8-methoxypsoralen (250 mg) in dry tetrahydrofuran (60 mL) was added. The solution was stirred at room temperature overnight. The solvent was removed by rotary evaporation, and the residual solid dissolved in dichloromethane, washed with dilute HCl then sodium carbonate solution. The organic layer was collected, dried over sodium sulfate, filtered and evaporated to dryness on a rotary evaporator. The crude residue was chromatographed on silica using methanol/dichloromethane (2%) and the major green band collected and evaporated. The residue, 8 Methoxypsorapyropheophoribide (Structure I below), was crystallized from dichloromethane/methanol.

EXAMPLE 2

Meso-Pyropheophorbide linked 8-MOP. (8-MOP MPPhe)

Meso-Pyropheophorbide (300 mg) was dissolved in dry tetrahydrofuran (100 mL) and 1,3-dicyclohexylcarbodiimide (100 mg) and dimethylaminopyridine (100 mg) were added. After stirring at room temperature for 15 min., a solution of 5-aminomethyl-8-methoxypsoralen (250 mg) in dry tetrahydrofuran (60 mL) was added. The solution was stirred at room temperature overnight. The solvent was removed by rotary evaporation, and the residual solid dissolved in dichloromethane, washed with dilute HCl then sodium carbonate solution. The organic layer was collected, dried over sodium sulfate, filtered and evaporated to dryness on a rotary evaporator. The crude residue was chromatographed on silica using methanol/dichloromethane (2%) and the major green band collected and evaporated. The residue, 8-Methoxymesopyropeophoribide (Structure II below), was crystallized from dichloromethane/methanol.

EXAMPLE 3

2-(1-Hexyloxyethyl) pyropheophorbide linked 8-MOP. (8-MOP HPPhe)

2-(1-Hexyloxyethyl) pyropheophorbide (200 mg) was dissolved in dry tetrahydrofuran (100 mL) and 1,3-dicyclohexylcarbodiimide (100 mg) and dimethylaminopyridine (100 mg) were added. After stirring at room temperature for 15 min., a solution of 5-aminomethyl-8-methoxypsoralen (170 mg) in dry tetrahydrofuran (60 mL) was added. The solution was stirred at room temperature overnight. The solvent was removed by rotary evaporation, and the residual solid dissolved in dichloromethane, washed with dilute HCl then sodium carbonate solution. The organic layer was collected, dried over sodium sulfate, filtered and evaporated to dryness on a rotary evaporator. The crude residue was chromatographed on silica using methanol/dichloromethane (2%) and the major green band collected and evaporated. The residue, 8-MOP HPPhe (Structure III), was crystallized from dichloromethane/methanol.

EXAMPLE 4

Octaethylbenzochlorin linked 8-MOP. (8-MOP OEBCS)

To a stirred solution of octaethylbenzochlorin sulfonylchloride (300 mg) in dry dichloromethane (50 mL), was added 5-aminomethyl-8-methoxypsoralen (170 mg) in dry dichloromethane (20 ml) and dry triethylamine (0.1 mL). The resulting solution was stirred at room temperature for 1 hr and the solvent removed by rotary evaporation. The crude residue was columned on silica using dichloromethane and the major grey band collected and recrystallized from dichloromethane/methanol to give the title compound (Stucture IV below).

EXAMPLE 5

Zinc octaethylbenzochlorin linked 8-MOP. (8-MOP ZnOEBCS)

To a stirred solution of octaethylbenzochlorin sulfonylchloride (300 mg) in dichloromethane (50 mL), was added 5-aminomethyl-8-methoxypsoralen (150 mg) in dichloromethane (20 ml) and dry triethylamine (0.1 mL). The resulting solution was stirred at room temperature for 1 hr. Zinc acetate (200 mg) dissolved in methanol (10 mL) was added to the reaction solution and the solution was warmed on a hot water bath until metallation of the benzochlorin was complete by Uv/vis spectroscopy (as seen by a band I absorption at 673 nm). The solvent was then removed by rotary evaporation and the crude residue redissolved in dichloromethane (5 mL) and chromatographed on silica using dichloromethane. The major green band collected and recrystallized from dichloromethane/methanol to give the title compound (Structure V below).

EXAMPLE 6

Cu iminium octaethylbenzochlorin linked 8-MOP. (8-MOP Cu Im OEBCS)

To copper octaethylbenzochlorin sulfonic acid (300 mg) dissolved in dichloromethane (100 mL) was added (chloromethylene) dimethylammonium chloride (500 mg) and the solution stirred overnight at room temperature, protected from moisture. The solution was poured into ice cold water quickly, the organic layer washed with water rapidly, separated and dried over sodium sulfate. The solution was filtered to remove sodium sulfate and 5-aminomethyl-8-methoxypsoralen (200 mg) in dichloromethane (20 mL) was added. The solution was stirred for 20 minutes at room temperature, then poured into water. The organic layer was washed with dilute HCl and dried over sodium sulfate. The solution was filtered and evaporated to dryness. The resulting reside was chromatographed on silica using 2% methanol/dichloromethane and the major green band collected and evaporated. The title compound (Structure VI below) was obtained as a green powder by precipitation from dichloromethane/hexane.

EXAMPLE 7

Indium texaphyrin linked 8-MOP. (8-MOP InT)

To a solution of Indium texaphyrin-16-carboxylic acid (200 mg) was dissolved in dry terahydrofuran (50 mL) and 1,3-dicyclohexylcarbodiimide (50 mg) and dimethylaminopyridine (50 mg) added. After stirring at room temperature for 15 min., a solution of 5-aminomethyl-8-methoxypsoralen (100 mg) in dry terahydrofuran (20 mL) was added. The solution was stirred under argon at room temperature overnight. The solvent was removed by rotary evaporation, and the residual solid dissolved in dichloromethane and washed with dilute HCl and finally with water. The organic phase was separated, dried over sodium sulfate, revaporated under reduced pressure and chromatographed on silica using methanol/dichloromethane (2%). The major green band was collected and evaporated. The residue, 8-MOP InT (Structure VIII below), was crystallized from dichloromethane/hexane.

EXAMPLE 8

Protoporphyrin linked 8-MOP. (8-MOP PP)

Protoporphyrin (200 mg) was dissolved in oxalyl chloride (3 mL) and the solution warmed at 40° C. for 1 hr, while being protected from moisture. The excess oxalyl chloride was removed under high vacuum and dry dichloromethane (5 mL) was added. This was also removed under high vacuum, to give a purple residue that was protected from moisture via a drying tube. Dry dichloromethane (10 mL) and dry triethylamine (1 mL) were added to the residue, followed by a solution of 5-aminomethyl-8-methoxypsoralen (160 mg) in dry dichloromethane (20 mL). The solution was stirred overnight, protected from moisture via a drying tube. The solution was then poured into water and the organic phase washed well with water, collected and dried over sodium sulfate. After filtration and evaporation to dryness, the resulting residue was columned on silica using 2% acetone/dichloromethane as eluent. The major red band was collected and recrystallized from dichloromethane/methanol to yield the title compound VIII.

EXAMPLE 9

Tetraphenylporphyrin linked 8-MOP. (8-MOP TPP)

Meso-terakis-(4'-carboxyphenyl) porphyrin (200 mg) was dissolved in oxalyl chloride (5 mL) and the solution warmed at 40° C. for 1 hr, while being protected from moisture. The excess oxalyl chloride was removed under high vacuum and dry dichloromethane (5 mL) was added. This was also removed under high vacuum, to give a green residue that was protected from moisture via a drying tube. Dry dichloromethane (10 mL) and dry triethylamine (1 mL) were added to the residue and a solution of 5-aminomethyl-8-methoxypsoralen (400 mg) in dry dichloromethane (20 mL) was added. The solution was stirred overnight, protected from moisture via a drying tube. The solution was then poured into water and the organic phase washed well with water, collected and dried over sodium sulfate. After filtration and evaporation to dryness, the resulting residue was columned on silica using 2% acetone/dichloromethane as eluent. The major red band comprised 8-MOP TPP (Structure IX) and was collected and recrystallized from dichloromethane/methanol.

EXAMPLE 10

2,8,12,18-Tetraethyl-3,7,13,17-tetramethyl-5,15-bis(2'-furan) porphyrin. (5,15-DFP)

4,4'-Diethyl-3,3'-dimethyl-2,2'-dipyrrylmethane (4.0 g) and 2-furaldehyde (1.67 g) were dissolved in methanol (100 mL) and the solution deaerated by bubbling with argon for 15 min. 4-Toluenesulfonic acid (0.95 g) was added and the solution stirred for 2 hrs in the dark, then refrigerated overnight. The precipitated porphyrinogen was collected, washed with ice cold methanol (20 mL) and resuspended in methanol (100 mL). o-Chloranil (6.0 g) was added and the solution stirred in the dark for 2 hrs. Triethylamine (2 mL) was added and the precipitated porphyrin was collected by filtration, washed well with methanol and dried under high vacuum. The porphyrin was recrystallized from dichloromethane/methanol to yield the title compound (X).

EXAMPLE 11

Texas red linked 8-MOP. (8-MOP TR)

Sulforhodamine 101 acid chloride (200 mg) was dissolved in dry tetrahydrofuran (100 mL) and 5-aminomethyl-8-methoxypsoralen (100 mg) added, followed by triethylamine (0.1 mL). The solution was left overnight at room temperature. The following day the solution was evaporated to dryness, redissolved in dichloromethane and columned on silica using 2% methanol/dichloromethane as eluent. The major fluorescent red fraction was collected and evaporated to dryness. The residue, comprising 8-MOP TR (Structure XI) was recrystallized from dichloromethane/hexane.

EXAMPLE 12

Rhodamine B linked 8-MOP. (8-MOP RB)

Sulforhodamine B acid chloride (200 mg) was dissolved in dry tetrahydrofuran (100 mL) and 5-aminomethyl-8-methoxypsoralen (100 mg) added, followed by dry triethylamine (0.1 mL). The solution was left overnight at room temperature. The following day the solution was evaporated to dryness, redissolved in dichloromethane and columned on silica using 2% methanol/dichloromethane as eluent. The major fluorescent red fraction was collected and evaporated to dryness. The residue (Structure XII) was recrystallized from dichloromethane/hexane.

EXAMPLE 13

Porphocyanine linked 8-MOP. (8-MOP Pocy)

2,3,21,22-tetraethyl-12-(4'-carboxyphenyl) porphocyanine (200 mg) was dissolved in dry tetrahydrofuran (100 mL) and 1,3-dicyclohexylcarbodiimide (100 mg) and dimethylaminopyridine (100 mg) were added. After stirring at room temperature for 15 min., a solution of 5-aminomethyl-8-methoxypsoralen (300 mg) in dry tetrahydrofuran (60 mL) was added. The solution was stirred at room temperature overnight. The solvent was removed by rotary evaporation, and the residual solid dissolved in dichloromethane, washed with dilute HCl then sodium carbonate solution. The organic layer was collected, dried over sodium sulfate, filtered and evaporated to dryness on a rotary evaporator. The crude residue was chromatographed on silica using methanol/dichloromethane (2%) and the major green band collected and evaporated. The residue (Structure XIII) was crystallized from dichloromethane/methanol.

EXAMPLE 14

Phthalocyanine linked 8-MOP. (8-MOP Pth)

Phthalocyanine tetra sulfonate (200 mg) was dissolved in phosphorus oxychloride (20 mL) and the solution refluxed for 2 hrs. The excess phosphorus oxychloride was removed by rotary evaporation and the residue dissolved in dry, cold pyridine (10 mL). A solution of 5-aminomethyl-8-methoxypsoralen (300 mg) in dry pyridine (60 mL) was added. The solution was stirred at room temperature overnight. The solvent was removed by rotary evaporation, and the residual solid dissolved in dichloromethane, washed with dilute HCl then sodium carbonate solution. The organic layer was collected, dried over sodium sulfate, filtered and evaporated to dryness on a rotary evaporator. The crude residue was chromatographed on silica using methanol/dichloromethane (5%) and the major green band collected and evaporated. The residue (Structure XIV) was crystallized from dichloromethane/methanol.

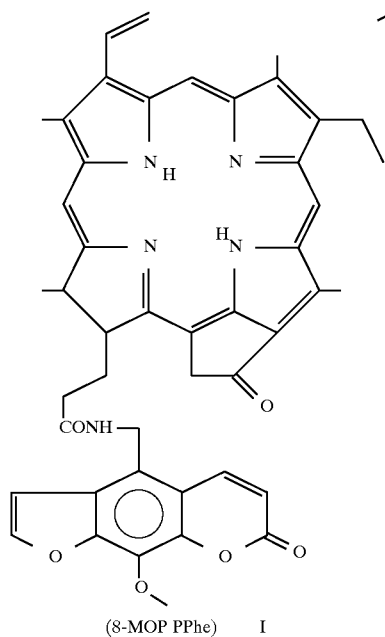
(8-MOP PPhe)　I
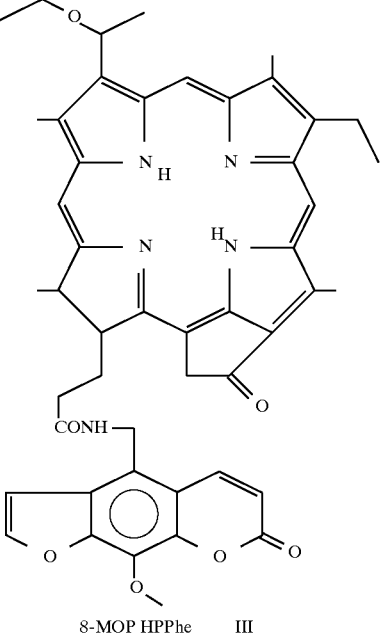
8-MOP HPPhe　III
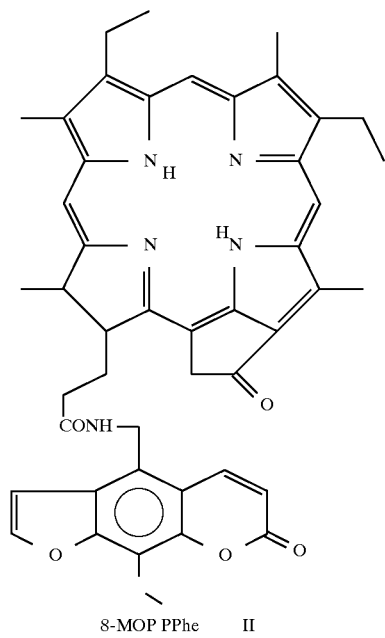
8-MOP PPhe　II
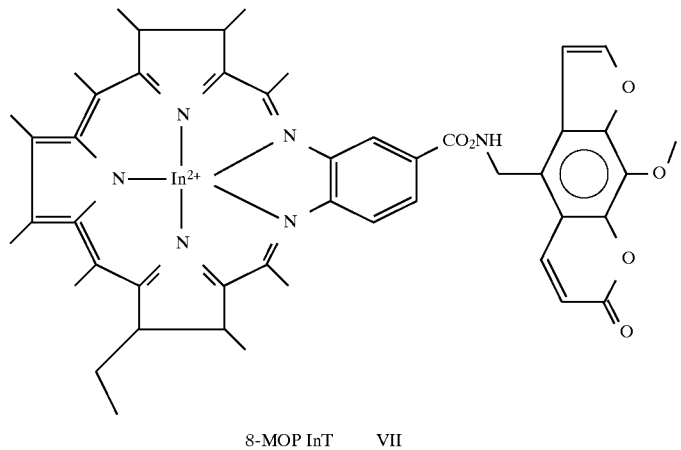
8-MOP InT　VII

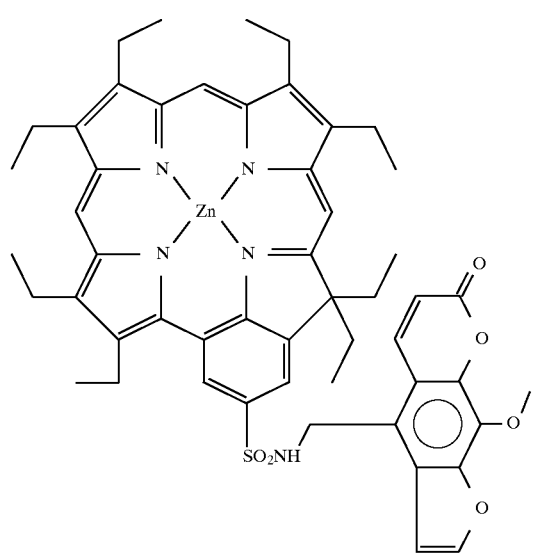
8-MOP ZnOEBCS    V
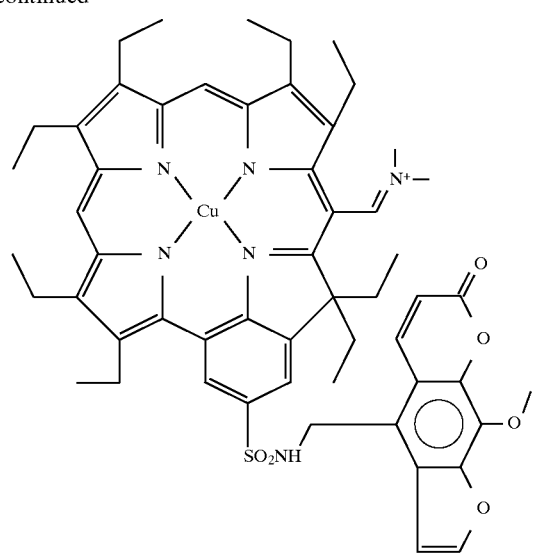
8-MOP Cu Im OEBCS    VI
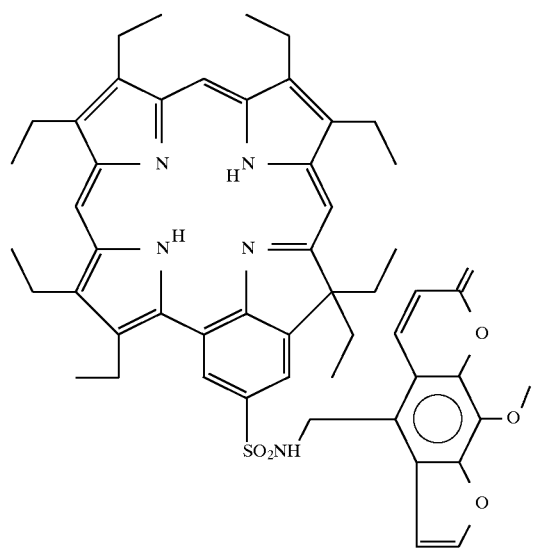
8-MOP OEBCS    IV
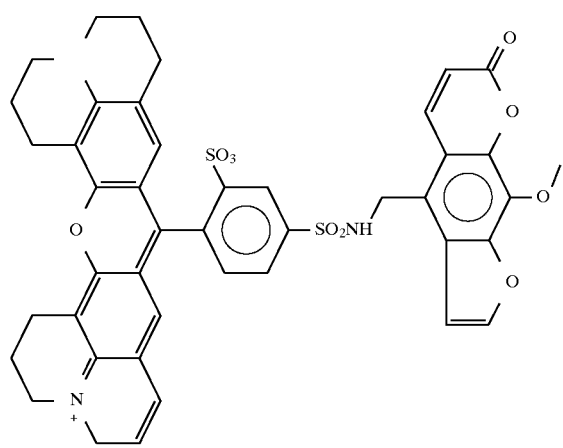
8-MOP TR    XI
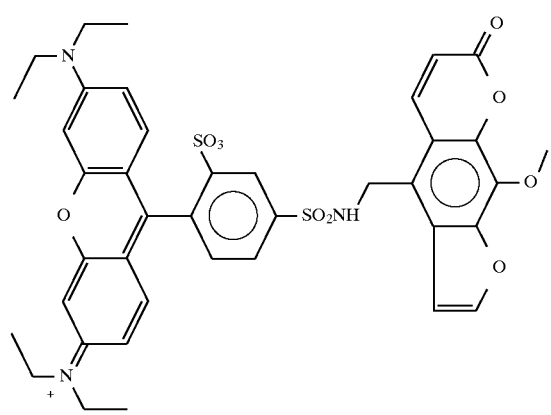
8-MOP RB    XII -continued
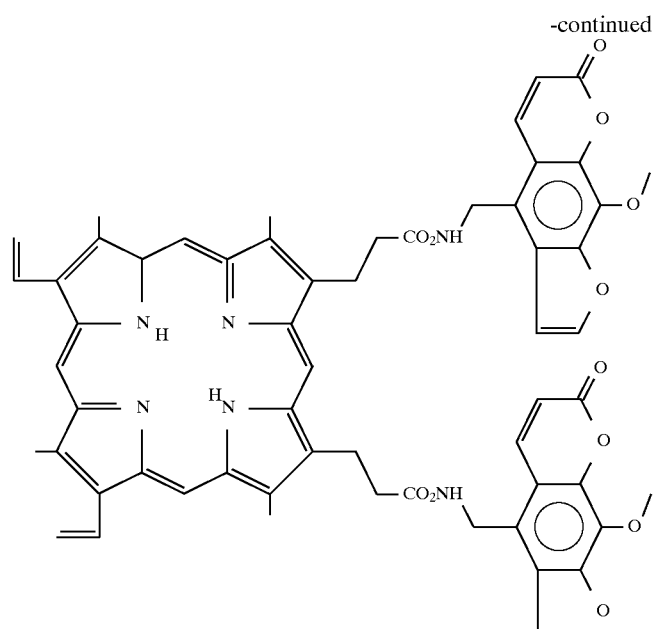
8-MOP PP    VIII
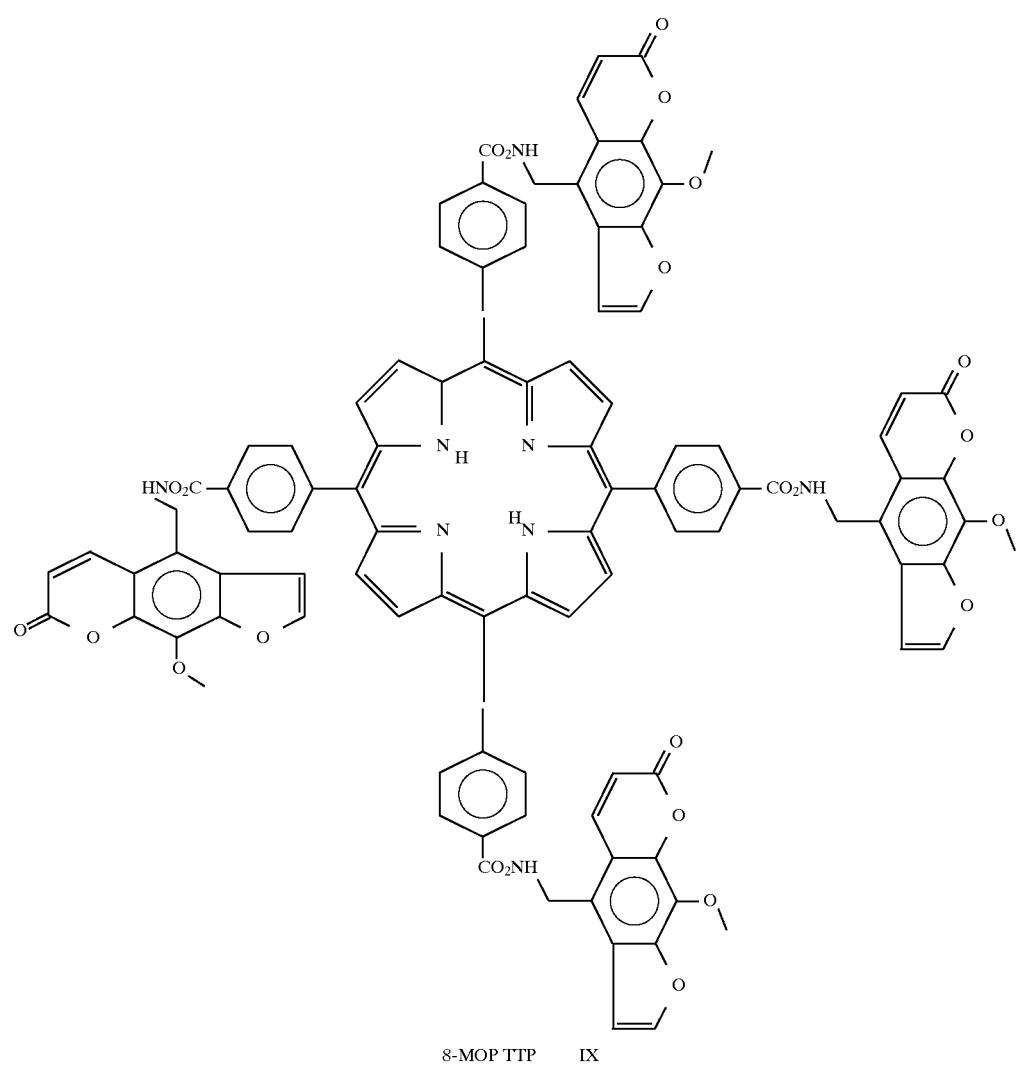
8-MOP TTP    IX

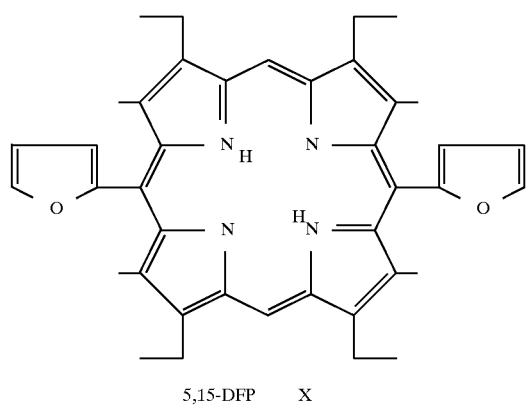

5,15-DFP    X

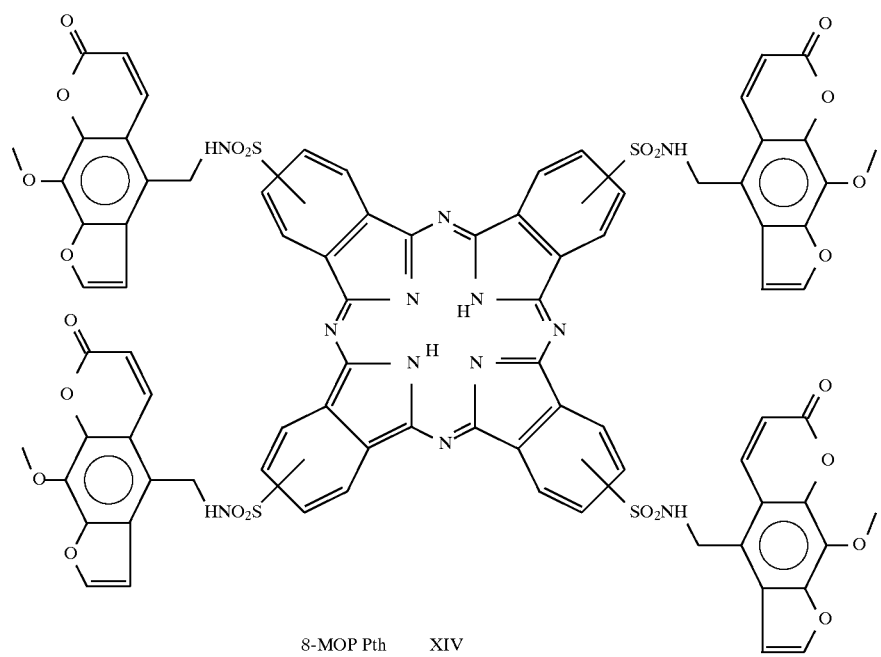

8-MOP Pth    XIV

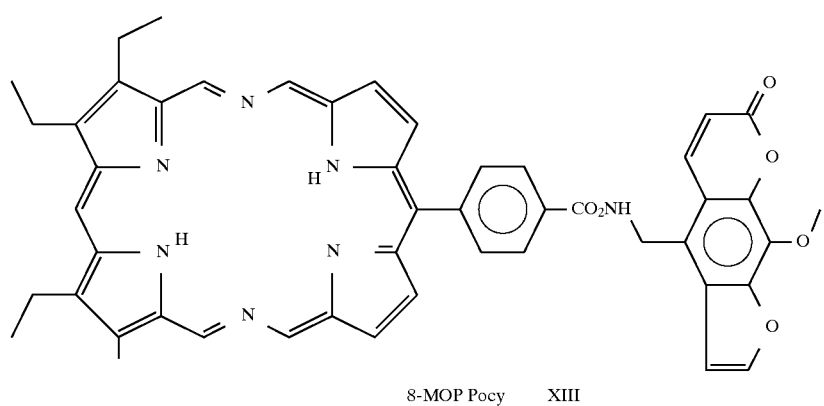

8-MOP Pocy    XIII

The preceding super-class of photosensitizing compounds may be characterized by: a) a furocoumarin attached to a Reactive Oxygen Producing Photosensitizer type compound, F-ROPP; b) a furocoumarin sub-component attached to a ROPP, FS-ROPP; c) a cationic furocoumarin attached to an ROPP (neutral or cationic), to produce either CF-ROPP or CFS-ROPP; d) a cationic ROPP attached to a furocoumarin (neutral or cationic); e) any one of the above compounds wherein the ROPP is metalized; and f) a furocoumarin conjugated with a light emitting photosensitizer, F-LEP.

The foregoing super-class of conjugated compounds can be used to treat a variety of diseases such as atherosclerosis, restenosis, cancer, cancer precursors, non-cancerous hyperproliferative diseases, psoriasis, macular degeneration, glaucoma, and certain viruses. These compounds are light activatable drugs which may or may not be photodynamically active (i.e. produce singlet oxygen and/or oxygen radicals to mediate cytotoxicity), but will be photoactive (i.e. exhibit photochemical cross-linking with DNA or RNA or the production of monoadducts of the compound therewith) to modulate the metabolic activity of cells. More specifically, these novel photoactive compounds will retain the ability of the ROPP or LEP to localize to a greater extent in the target tissue and the ability of the furocoumarin (such as psoralen) to intercalate into target tissue DNA and form cross-linked and/or monoadducts adducts upon the addition of light energy.

Previous studies indicate that utilizing a cationic ROPP or LEP to synthesize a CF-ROPP or CF-LEP facilitates the intercalation of the compound into target cell DNA. Once the F-ROPP or CF-ROPP is localized in target cells, light activation can be used therapeutically and/or diagnostically. The use of these novel compounds for the detection and/or treatment and the prevention of restenosis and intimal hyperplasia following cardiac transplantation surgery (or AV shunt procedures such as dialysis) is an exemplary application which is discussed in particular detail to teach and illustrate a use for the invention, but it should be kept in mind that such an application is illustrative and should not be construed as a limitation of this invention.

For example, another application for the photosensitizer compounds described herein is the light activated treatment of a target tissue which does not selectively concentrate either ROPPs or furocoumarins. An F-ROPP, selected as described below from the super-class of compounds described above, can be administered systemically to a biological organism, which organism could be an animal, a plant or even a single cell or a polynucleic acid fragment. Following systemic administration of the F-ROPP, and while the F-ROPP is present in the animal's serum, a light source operating at a strong absorption wavelength of the furocoumarin component of the F-ROPP, is directed toward the volume of target tissue in which high concentrations of the F-ROPP are desired. The selection of the particular furocoumarin used in the F-ROPP is preferably a species which creates mono-adducts with polynucleic acids when activated with UV or short wavelength visible light. By administering the activating light to the target tissue, mono-adducts of F-ROPPs with DNA and RNA are formed. Increasing the intensity of the activating light delivered to the target tissue increases the DNA-bound F-ROPP therein. When the F-ROPP reaches the desired concentration in the target tissue, a longer wavelength of light which activates the ROPP portion of the F-ROPP may be used to photoactivate the cell bound F-ROPP in the target tissues to selectively destroy or modify the target tissue. In effect, the F-ROPP creates a light-induced selectivity of the F-ROPP for binding to the target tissue because only the target tissue is illuminated with the shorter wavelength of light thereby causing covalent bonding of F-ROPP only in the DNA/RNA of the target tissue.

While particular embodiments of the present invention have been illustrated and described, it would be obvious to those skilled in the art that various other changes and modifications can be made without departing from the spirit and scope of the invention. It is therefore intended to cover in the impending claims all such changes and modifications that are within the scope of this invention.

What we claim is:

1. A photoactive composition for treating diseased target tissue cells within an organism, said photoactive composition having the form R—R' wherein R is a photoactivatable furocoumarin compound which covalently bonds to DNA within target tissue cells when the furocoumarin compound is photoactivated with light having a first wavelength within the ultraviolet region of the electromagnetic spectrum, and R' is a photosensitive compound having a fused tetrapyrrolic core which interferes with normal cellular activity within the target tissue when photoactivated with light having a second wavelength within the visible or infrared region of the spectrum.

2. The photoactive composition of claim 1 wherein R forms a monoadduct with cellular DNA within the target tissue when photoactivated with said light having said first wavelength.

3. The photoactive compound of claim 1 wherein R produces crosslinking of target tissue cellular DNA when photactivated by said light having a first wavelength.

4. The photoactive compound of claim 2 wherein R' is a reactive oxygen producing photosensitizer compound.

5. The photoactive compound of claim 3 wherein R' is a reactive oxygen producing photosensitizer compound.

\* \* \* \* \*

UNITED STATES PATENT AND TRADEMARK OFFICE
CERTIFICATE OF CORRECTION

PATENT NO. : 5,773,609
DATED : June 30, 1998
INVENTOR(S) : Byron Robinson et al.

It is certified that error appears in the above-indentified patent and that said Letters Patent is hereby corrected as shown below:

On the title page: Item [54] and Column 1, line 3,
Please delete the title and substitute therefor the new title as follows:
--COMPOSITIONS FORMING AN ADDUCT WITH DNA FOR PERFORMING PDT--

Signed and Sealed this

Thirtieth Day of March, 1999

Attest:

Attesting Officer

Q. TODD DICKINSON

Acting Commissioner of Patents and Trademarks